United States Patent
Gaylord (12)

(10) Patent No.: US 6,659,971 B2
(45) Date of Patent: Dec. 9, 2003

(54) SHOULDER ABDUCTION SLING

(75) Inventor: Eric Lee Gaylord, Matthews, NC (US)

(73) Assignee: Medical Specialties, Inc., Charlotte, NC (US)

( * ) Notice: Subject to any disclaimer, the term of this patent is extended or adjusted under 35 U.S.C. 154(b) by 0 days.

(21) Appl. No.: 10/107,841

(22) Filed: Mar. 27, 2002

(65) Prior Publication Data

US 2003/0187373 A1 Oct. 2, 2003

(51) Int. Cl.[7] .................................................. A61F 5/00
(52) U.S. Cl. ............................................. 602/4; 602/13
(58) Field of Search ....................... 602/4, 13; 224/157, 224/158; 5/89; 294/140, 152, 156

(56) References Cited

U.S. PATENT DOCUMENTS

| | | | |
|---|---|---|---|
| 114,615 A | | 5/1871 | Smitley |
| 1,808,422 A | * | 6/1931 | MacDonald |
| 4,198,964 A | * | 4/1980 | Honneffer |
| 4,232,664 A | * | 11/1980 | Blatt |
| 4,355,635 A | | 10/1982 | Bihl et al. |
| 4,572,172 A | * | 2/1986 | Williams |
| 4,598,701 A | * | 7/1986 | Schaefer |
| 4,625,719 A | * | 12/1986 | Chambers |
| 4,834,082 A | | 5/1989 | Ghadiali |
| 4,836,195 A | | 6/1989 | Berrehail |
| 4,896,660 A | | 1/1990 | Scott |
| 5,358,470 A | * | 10/1994 | Johnson |
| 5,385,536 A | | 1/1995 | Burkhead et al. |
| 5,464,383 A | * | 11/1995 | Padden et al. |
| 5,538,499 A | | 7/1996 | Schwenn et al. |
| 5,678,739 A | * | 10/1997 | Darling et al. |
| 5,772,617 A | * | 6/1998 | Lay |
| D396,291 S | | 7/1998 | Bakes |
| 6,102,877 A | * | 8/2000 | Joslin |

FOREIGN PATENT DOCUMENTS

EP 0904752 A1 * 9/1997

OTHER PUBLICATIONS

Brace Support; *Breg Shoulder Abduction Pillow*; # BR–01850; http://bracesupport.com/breg/abduction.htm.
Brace Support; *Brace Slingshot Arm/Shoulder Immobilizer*, # BR–08400 & # BR–08401; http://bracesupport.com/breg/shoulder.htm.
Dj Orthopedics, LLC; *Never Stop Getting Post–Op Fracture Bracing: UltraSling*; wysiwyg://23/http://www.djortho-.com/products/DonJoy/patient/detail.asp?id=124.
Dj Orthopedics, LLC; *Never Stop Getting Better Post–Op Fracture Bracing: UltraSling II*; wysiwyg://18/http://www.djortho.com/products/DonJoy/patient/detail.asp?id=123.
Dj Orthopedics, LLC; *Never Stop Getting Better Post–Op Fracture Bracing: UltraSling II AB*; wysiwyg://20/http://www.djortho.com/products/DonJoy/patient/detail.asp?id=145.

* cited by examiner

*Primary Examiner*—Nicholas D. Lucchesi
*Assistant Examiner*—Lalita M. Hamilton
(74) *Attorney, Agent, or Firm*—Summa & Allan, P.A.

(57) ABSTRACT

An adjustable abduction apparatus, including a cushion for being received against the torso, a sling pouch attached to the cushion for maintaining a limb and shoulder of the wearer in an abducted position, and a support connected to the pouch for immobilizing the limb and shoulder in the abducted position and distributing the weight of the abducted limb evenly across the torso of the wearer. A waist strap is carried by the cushion and releasaby secures the apparatus against the torso. A back strap interconnects the waist strap and the sling pouch and extends therebetween generally parallel to the spinal column of the wearer for supporting the sling pouch and maintaining the limb and shoulder in the abducted position.

25 Claims, 11 Drawing Sheets

SHOULDER ABDUCTION SLING

TECHNICAL FIELD AND BACKGROUND OF THE INVENTION

This invention relates to an abduction and immobilization device, or "shoulder abduction sling" for use by a patient in conjunction with post-operative and other types of rehabilitative care provided to the patient by an orthopedic surgeon, sports medicine professional, or other health care provider. Intended to provide immobilization and abduction to treat a wide range of conditions affecting the pectoral girdle, the shoulder abduction sling of the present invention is particularly suited for use as a part of a postoperative or post-injury rehabilitation program for arthroscopic procedures, rotator cuff tears, thermal capsulorrhapy or other procedures to treat capsular shifts or tears, subluxations, dislocations, and other shoulder instabilities.

One of the challenges faced by physicians and therapists in treating patients who are recovering from injury or surgery to the shoulder region is to provide a means of immobilizing and abducting the patient's affected arm and shoulder during recovery without severely compromising the comfort and overall mobility of the patient. While prior art devices exist for abducting injured upper limbs, such devices are inadequate in that they utilize straps that irritate the patient's neck and fail to adequately distribute the weight of the injured limb across the patient's upper body, abduction pillows that are uncomfortable and unnecessarily restrict the use of the abducted hand, and sling pouches that fail to account for differences in bone sizes among patients.

The invention of the present application overcomes the problems associated with prior art devices by providing a shoulder abduction sling that incorporates a unique support cushion strap assembly and sling pouch. In particular, the strap assembly of the shoulder abduction sling is specifically structured to prevent the discomfort associated with shoulder straps used on conventional abduction slings. A conventional shoulder strap is connected directly to the sling pouch adjacent the wearer's elbow, extends across the wearer's back, passes over the wearer's uninjured shoulder adjacent the neck, and connects to the other end of the sling pouch adjacent the wearer's hand. This type of connection causes the strap to exert a painful lateral force against the wearer's neck when the conventional sling is worn. In contrast, the strap assembly of the present invention provides a set of three straps that cooperate together to distribute the weight of the abducted arm across the wearer's back and away from the wearer's neck region. The first ends of the straps are connected to one of either the sling pouch or the abduction cushion. The second ends of the straps are connected to a ring that is positioned on the patient's back adjacent the patient's uninjured scapula. This unique configuration of straps lifts and supports the abducted forearm and elbow without requiring any straps to be placed near the neck, and thus eliminates the neck pain associated with prior art devices. Although one of the straps does cross the patient's uninjured shoulder, the unique distribution of straps and placement of the ring on the wearer's back causes the strap on the wearer's uninjured shoulder to be pulled away from the wearer's neck.

The present invention also utilizes an abduction cushion having a unique shape designed to accommodate the anatomy of the wearer's forearm and hand. In particular, the surface of the cushion is contoured to account for the non-vertical angle of the humerus, which enhances the overall comfort of the wearer. Furthermore, unlike prior art devices which include thumb holders that restrict hand movement, the cushion included with the present invention does not require any type of thumb support, but instead has a face against which the wearer's hand rests that is specifically shaped to allow the wearer a wider range of hand motion. This in turn permits the wearer to use his or her hand to perform a broader range of tasks while wearing the sling, such as holding a soft drink can while opening it or grasping a jar to unscrew its cap. Any movement of the forearm within the sling that would have otherwise been prevented by using a conventional thumb holder is addressed by providing a closure strap which wraps around the open edges of the sling pouch where the forearm meets the elbow. This unique closure strap prevents the wearer's forearm from sliding forward in the sling without resorting to restricting movement of the thumb, fingers and hand.

SUMMARY OF THE INVENTION

Therefore, it is an object of the present invention to provide a shoulder abduction sling having a strap system that distributes the weight of the abducted upper limb across a wearer's back rather than over the uninjured shoulder and against the wearer's neck.

It is another object of the present invention to provide a shoulder abduction sling that can be worn on either the left or right arm.

It is another object of the present invention to provide an abduction sling having an adjustable strap system so that the sling can be precisely fitted to ensure that adequate support and the proper degree of abduction is provided to the shoulder region.

It is another object of the present invention to provide an abduction sling having an abduction cushion shaped to accommodate the contours of the humerus and associated musculature.

It is another object of the present invention to provide an abduction apparatus that preserves the mobility of the abducted hand.

These and other objects of the present invention are achieved in the preferred embodiments disclosed below by providing an adjustable abduction apparatus. The abduction apparatus includes a cushion for being received against the torso of the wearer, and a sling pouch for receiving the limb of the wearer therein. The sling pouch is releasably attached to the cushion and cooperates therewith for maintaining the limb and shoulder in the abducted position. A support assembly immobilizes the limb and shoulder in the abducted position and distributes the weight of the abducted limb evenly across the shoulders of the wearer. The support assembly includes a waist strap carried by the cushion for releasably securing the apparatus against the torso, and a back strap interconnecting the waist strap and the sling pouch and extending therebetween along the back generally parallel to the spinal column. The back strap provides stabilizing support to the sling pouch for maintaining the limb in the abducted position.

According to one preferred embodiment of the present invention, a shoulder strap interconnects the back strap and the sling pouch and extends therebetween generally diagonally across the spinal column of the wearer.

According to another preferred embodiment of the invention, the waist strap is carried by the cushion for releasably securing the cushion against the torso.

According to yet another preferred embodiment of the invention, the waist strap is an elongate strap having an outer surface, a first end connected to a first lateral surface of the cushion, and a second end releasably connected to a second opposing lateral surface of the cushion for holding the cushion in place against the torso of the wearer.

According to yet another preferred embodiment of the invention, a first fastener is attached to the second lateral surface of the cushion and cooperates with a second fastener carried by the waist strap for holding the cushion in place against the torso of the wearer.

According to yet another preferred embodiment of the invention, the second fastener is a tongue carried by the waist strap and the first fastener is a complementary clasp for receiving the tongue therein.

According to yet another preferred embodiment of the invention, a third fastener is releasably attached to the second end of the waist strap and cooperates with the outer surface of the waist strap for releasably securing the second end of the waist strap thereto.

According to yet another preferred embodiment of the invention, the back strap includes upper and lower straps having respective first and second ends. The first ends are joined together at a common point for being positioned on the wearer's back.

According to yet another preferred embodiment of the invention, the shoulder strap is connected to the back strap at the common point.

The common point is preferably a ring member.

According to yet another preferred embodiment of the invention, the sling pouch includes a closed end defining a lower opening for receiving the wearer's elbow therethrough and an open end for receiving the wearer's hand therethrough.

According to yet another preferred embodiment of the invention, the sling pouch includes opposing upper edges defining an upper opening through which the wearer's arm is received for positioning the arm within the pouch, and a side edge defining the open end.

According to yet another preferred embodiment of the invention, a closure strap is included for releasably interconnecting the upper edges for maintaining the wearer's forearm in a stationary position within the pouch.

According to yet another preferred embodiment of the invention, the shoulder strap is releasably connected by a fourth fastener to the sling pouch adjacent the lower opening.

According to yet another preferred embodiment of the invention, the fourth fastener includes a snap hook connected to the shoulder strap and a complementary D-ring connected to an upper edge of the sling pouch adjacent the lower opening. The D-ring is adapted for receiving the snap hook therethrough.

According to yet another preferred embodiment of the invention, the shoulder strap has an outer surface and first and second ends. The first end is connected to the first strap. The second end is received through a complementary opening defined by the snap hook and is releasably attached to the outer surface of the shoulder strap, thereby permitting the length of the shoulder strap to be adjusted.

According to yet another preferred embodiment of the invention, a fifth fastener releasably connects the back strap to the sling pouch and cooperates therewith for defining the open end of the sling pouch.

According to yet another preferred embodiment of the invention, the upper edge of the sling pouch is integrally formed with a side edge of the sling pouch and cooperates with the side edge and the fifth fastener for defining the open end.

According to yet another preferred embodiment of the invention, the fifth fastener includes two loops connected to the upper edge of the sling pouch adjacent the open end. Each of the loops is adapted for receiving the second end of the back strap therethrough. A patch of hooked material is connected to the second end of the shoulder strap and cooperates with a complementary outer surface of the back strap for permitting the length of the back strap to be adjusted.

According to yet another preferred embodiment of the invention, a sixth fastener is attached to an anterior portion of the sling pouch adjacent the upper edge. The sixth fastener cooperates with a seventh fastener attached to a posterior portion of the sling pouch adjacent the upper edge for releasably connecting the anterior and posterior portions together, thereby stabilizing movement of the loops of the fifth fastener relative to the back strap.

According to yet another preferred embodiment of the invention, the sixth fastener is a patch of hooked material and the seventh fastener is a complementary patch of looped material.

According to yet another preferred embodiment of the invention, the sixth fastener is a patch of looped material and the seventh fastener is a complementary patch of hooked material.

According to yet another preferred embodiment of the invention, an elongate fastener releasably connects the sling pouch to the cushion.

According to yet another preferred embodiment of the invention, the elongate fastener includes two opposing hooked surfaces adapted for being releasably connected to respective complementary fibrous surfaces of the sling pouch and cushion.

According to yet another preferred embodiment of the invention, another adjustable abduction apparatus for abducting a limb and shoulder relative to the torso of a wearer is provided. The abduction apparatus includes a cushion for being received against the torso of the wearer for maintaining the limb and shoulder in an abducted position relative to the torso, and a sling pouch for receiving the limb therein. The sling pouch is releasably attached to the cushion and cooperates therewith for maintaining the limb and shoulder in the abducted position. A support assembly is releasably connected to the pouch and cushion for immobilizing the limb and shoulder in the abducted position and distributing the weight of the abducted limb evenly across the shoulders of the wearer. The support assembly includes a waist strap carried by the apparatus for releasably securing the apparatus against the torso, and a back strap interconnecting the waist strap and the sling pouch and extending therebetween generally parallel to the spinal column of the wearer. The back strap provides stabilizing support to the sling pouch for maintaining the limb in the abducted position.

According to yet another preferred embodiment of the invention, another adjustable abduction apparatus for abducting a limb and shoulder relative to the torso of a wearer is provided. The abduction apparatus includes a cushion for being received against the torso of the wearer for maintaining the limb and shoulder in an abducted position relative to the torso, and a sling pouch for receiving the limb therein. The sling pouch is releasably attached to the cushion and cooperates therewith for maintaining the limb and shoulder in the abducted position. A support assembly is releasably connected to the pouch and cushion for immobilizing the limb and shoulder in the abducted position and distributing the weight of the abducted limb evenly across the shoulders of the wearer. The support assembly includes a waist strap carried by the apparatus for releasably securing the apparatus against the torso, and a back strap interconnecting the waist strap and the sling pouch and extending therebetween generally parallel to the spinal column of the wearer. The back strap provides stabilizing support to the sling pouch for maintaining the limb in the abducted position. A shoulder strap interconnects the back strap and the sling pouch and extends therebetween generally diagonally across the spinal column of the wearer.

An embodiment of a method of according, to the invention is provided for abducting a limb and injured shoulder relative to the torso of a wearer. The method includes the step of providing an adjustable abduction apparatus. The apparatus includes a cushion for being received against the torso of the wearer and a sling pouch for receiving a limb of the wearer therein. The sling pouch is releasably attached to the cushion and cooperates therewith for maintaining the limb and shoulder of the wearer in an abducted position. A support assembly immobilizes the limb and shoulder in the abducted position and distributes the weight of the abducted limb evenly across the torso of the wearer. The support assembly includes a waist strap carried by the cushion for releasably securing the cushion against the torso and a back strap interconnecting the waist strap and the sling pouch and extending therebetween along the back generally parallel to the spinal column for providing stabilizing support to the sling pouch and maintaining the limb and shoulder in the abducted position. The method also includes the steps of positioning the cushion against the torso of the wearer, using the waist strap to releasably secure the cushion in place against the torso, positioning the limb of the wearer within the sling pouch, releasably attaching the sling pouch to the cushion, extending the back strap from the waist strap over the uninjured shoulder of the wearer to the sling pouch, and connecting the waist strap to the sling pouch.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
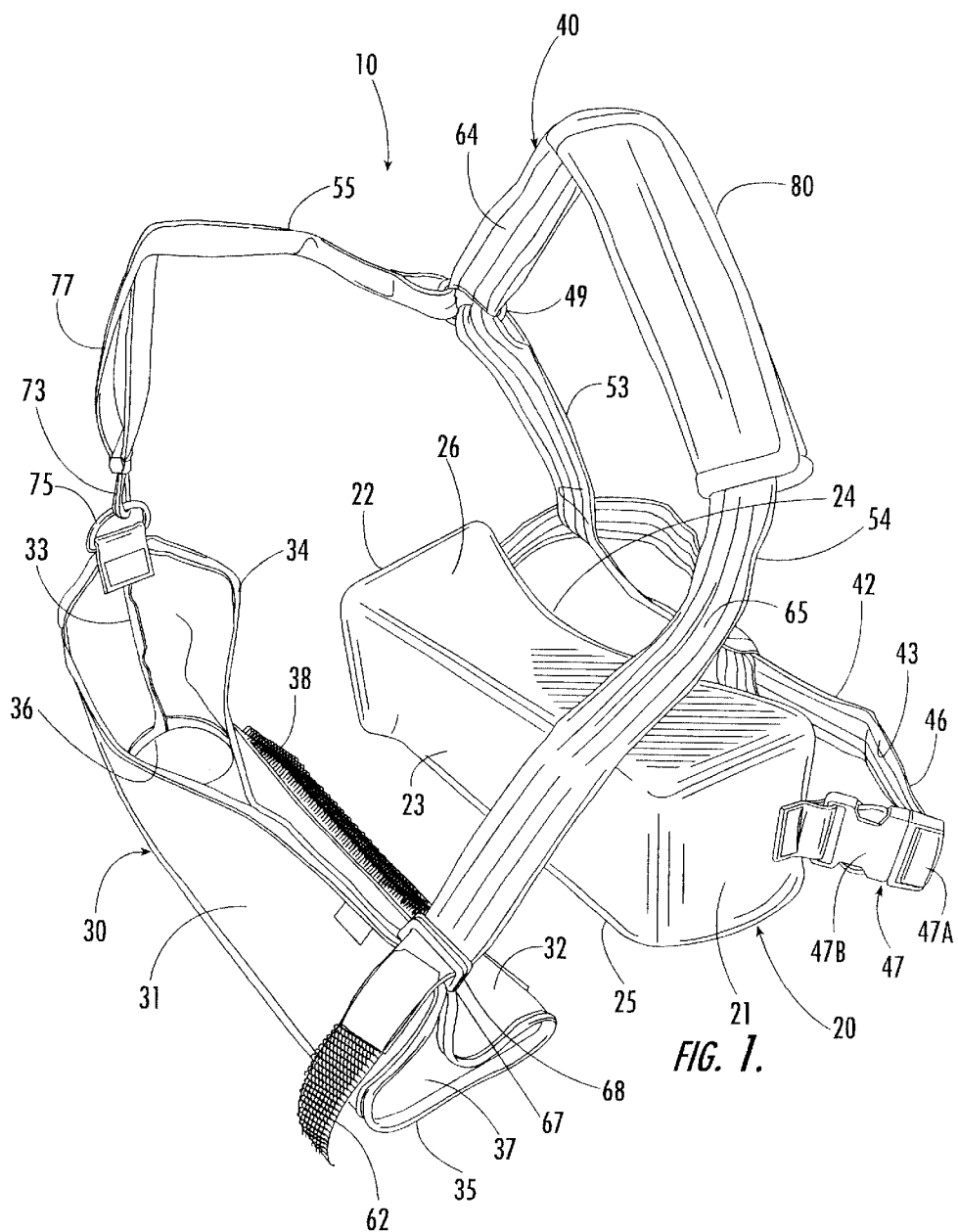
FIG. 1 is a perspective view of a shoulder abduction sling according to one preferred embodiment of the invention.

Referring now specifically to the drawings, an abduction device according to one embodiment of the present invention is illustrated in FIG. 1 and shown generally at reference numeral 10. The device 10 includes a cushion 20 that fits against a wearer's torso beneath the wearer's abducted forearm (See FIGS. 7 through 9). While the cushion 20 may be formed from any suitable materials, the cushion 20 is preferably formed from a flexible substance such as a foam material, and is covered with an elasticized or woven knitted material having a raised, fibrous surface. Furthermore, while the cushion 20 may have any suitable shape, the cushion 20 preferably has a polygonal shape and includes opposing lateral surfaces 21 and 22 that are integrally formed with anterior, posterior, inferior and superior surfaces 23, 24, 25 and 26, respectively. Lateral surface 22 is specifically contoured to accommodate and comfortably support the non-vertical angle of the humerus when the humerus is placed in an abducted position (See FIG. 8). In addition, lateral surface 21 is contoured to cooperate with the contour of anterior surface 23 to enhance the wearer's ability to use his or her hand while the hand is in the sling.

The abduction device 10 also includes a sling pouch 30. The pouch 30 is preferably formed from an elasticized or woven knitted material covered with a raised, fibrous surface like that used to cover the cushion 20. The pouch 30 is shaped to receive and support a wearer's forearm, and is formed from a single portion of material which is folded to form front and back panels 31 and 32, respectively. The front and back panels 31 and 32 are joined together at a side seam 33 to form respective upper and side edges 34 and 35, and a lower opening 36 and open end 37. An elongate fastener 38 is connected to the exterior of the back panel 32. The fastener 38 is covered on both sides with male hook fasteners (the opposite side of the fastener 38 is shown in FIG. 4) and is used to connect the back panel 32 to the anterior surface 23 of the cushion 20.

Figure 2:
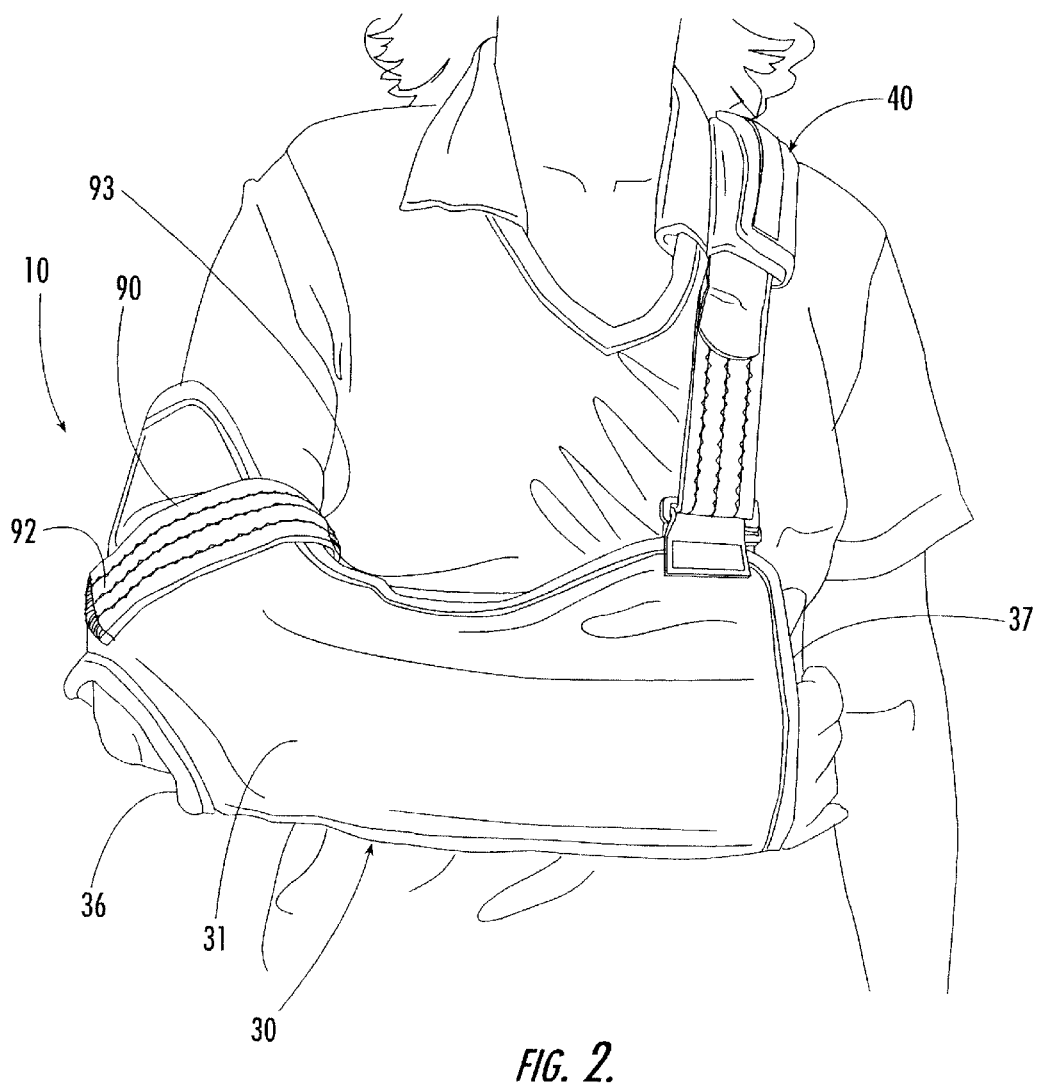
FIG. 2 is a forward environmental view of the shoulder abduction sling according to FIG. 1.
Figure 3:
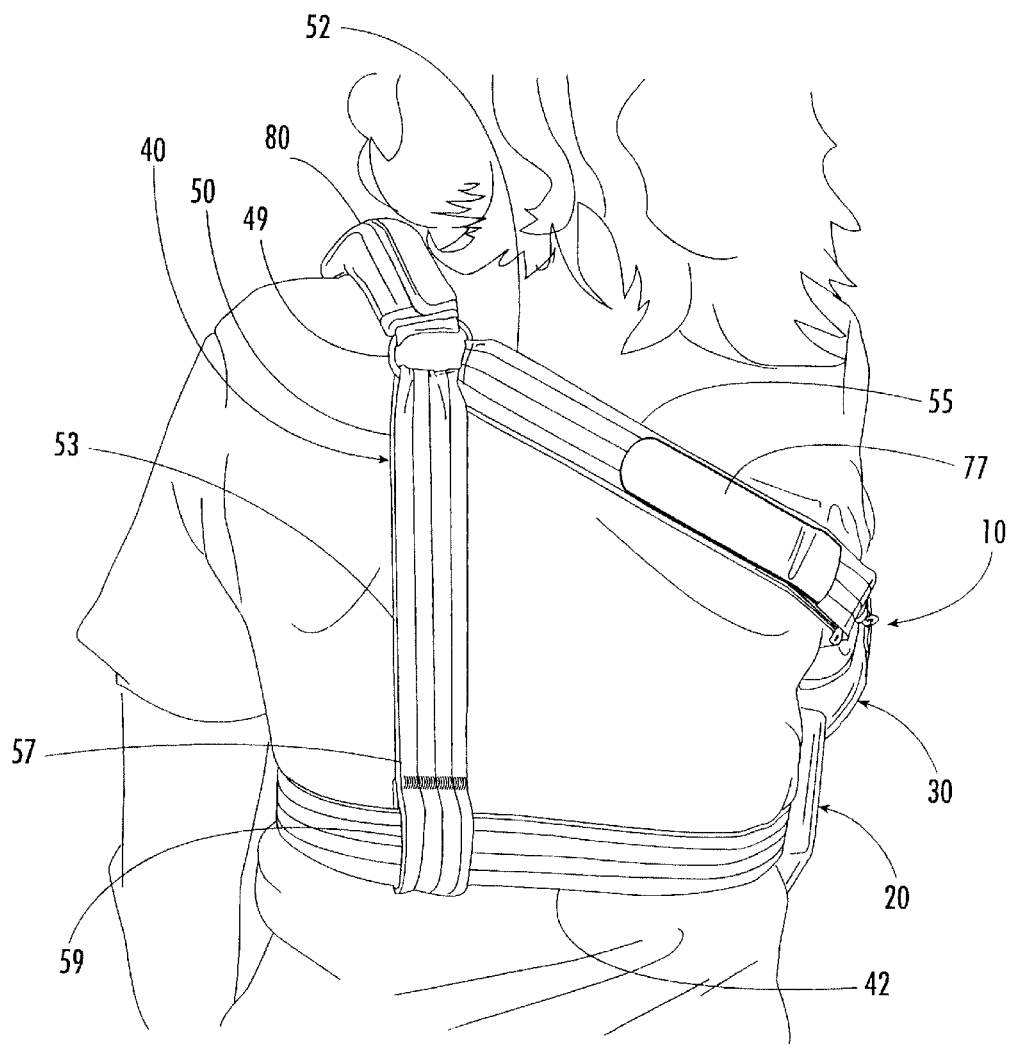
FIG. 3 is a rear environmental view of the shoulder abduction sling according to FIG. 1.

As is shown in FIG. 1, the abduction device 10 also includes a strap assembly 40. The strap assembly 40 is used to hold the pouch 30 and cushion 20 in place against the torso of the wearer (see FIG. 2). FIG. 3 shows the manner in which the strap assembly 40 extends across the shoulders and back and around the waist of the wearer to hold the cushion 20 and pouch 30 in place to ensure that the wearer's clavicular complex and arm are immobilized and maintained in an abducted position.

Figure 4:
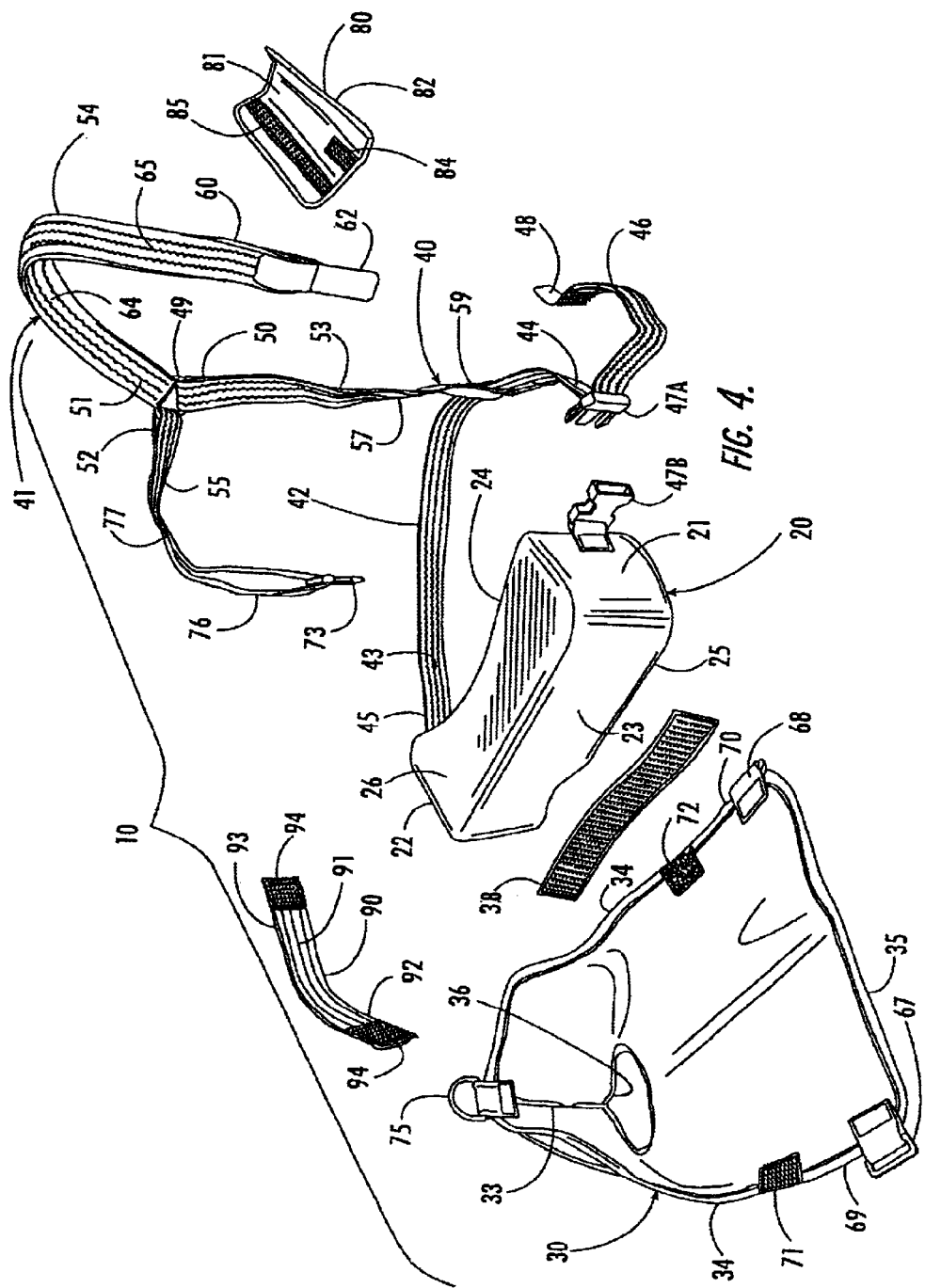
FIG. 4 is an exploded perspective view of the shoulder abduction sling according to FIG. 1 prior to assembly.

Referring now to FIG. 4, the components of the abduction device 10 are shown in detail. The strap assembly 40 includes a generally Y-shaped shoulder strap unit 41 connected to an elongate waist strap 42. Although the waist strap 42 may be formed from any suitable material, the waist strap 42 is preferably formed from an elasticized or woven knitted material covered with a raised fibrous surface like that used to form the pouch 30. The waist strap 42 has inner and outer surfaces 43 and 44, and first and second ends 45 and 46, respectively. The first end 45 is attached to the lateral surface 22 of cushion 20 (see FIG. 8). This permits the second end 46 of the waist strap 42 to extend across the wearer's back and beneath the wearer's uninjured arm, where it is then connected to lateral surface 21 (see FIGS. 1 and 7).

Referring again to FIG. 1, the waist strap 42 is connected to the opposing lateral surface 23 of the cushion 20 by a slide release buckle 47. Although the slide release buckle 47 is the preferred device for connecting the waist strap to the cushion 20, any other suitable connector may be used. As is shown in FIG. 4, the slide release buckle 47 includes a tongue member 47A which is carried by the waist strap 42. The tongue member 47A is received within a complementary clasp 47B, which is in turn attached to the lateral surface 21 of the cushion 20. The manner in which the tongue member 47A is positioned on the waist strap 42 allows the length of the waist strap 42 to be conveniently adjusted so that the posterior surface 24 of the cushion 20 fits snugly against the wearer's torso. As discussed in greater detail below with reference to FIG. 7, a removable fastener 48 is attached to the second end 46 of the waist strap 42 and is used to connect the second end 46 to the outer surface 44 after the length of the waist strap 42 has been adjusted.

Referring again to FIG. 4, the Y-shaped shoulder strap 41 includes a ring member 49 to which first ends 50, 51 and 52 of first, second and third divergent strap segments 53, 54 and 55 are connected. The first strap segment 53 has a second end 57 movably connected to the waist strap 42. The second end 57 forms a slotted opening 59 through which the waist strap 42 is threaded. This permits the first strap segment 53 to be moved along the waist strap 42 so that the strap segment 53 and ring member 49 are positioned in offset relation to the spinal column of the wearer (see FIG. 3).

As is shown in FIG. 4, the second strap segment 54 has a second end 60 to which a removable fastener 62 is attached. The second strap segment 54 also includes inner and outer surfaces 64 and 65, respectively, and is connected to the sling pouch 30 by threading the fastener 62 and second end 60 through two identical loop members 67 and 68 (see FIG. 1). As is shown in FIG. 4, the loop members 67 and 68 are connected to respective opposing terminal ends 69 and 70 of the upper edge 34 of the pouch 30 adjacent the side edge 35. As is discussed in greater detail below with respect to FIG. 6, connecting the second strap segment 54 to the pouch 30 in this manner causes the pouch 30 to be drawn against the anterior surface 23 of the cushion 20. The opposing terminal ends 69 and 70 of upper edge 34 of the pouch 30 are likewise drawn together to form the open end 37. Fastener 62 is then used to secure the second end 60 to the outer surface 65 of the second strap segment 54.

Referring again to FIG. 4, the pouch 30 also includes complementary male or female hook-and-loop fasteners 71 and 72. Fasteners 71 and 72 are attached to the interior of the pouch 30 along the upper edge 34 adjacent respective loop members 67 and 68. Fasteners 71 and 72 are joined together after the pouch 30, cushion 20 and second strap segment 54 have been oriented relative to one another and to the wearer. Fasteners 71 and 72 help to prevent inadvertent movement of the pouch 30, and loop members 67 and 68 after the length of second strap segment 54 has been adjusted and the second end 60 has been secured in position by fastener 62, and also help to keep the wearer's forearm in a stationary position within the pouch 30.

The third strap segment 55 of the shoulder strap 41 is connected to the pouch 30 by a relatable snap hook 73 and complementary D-ring member 75 (See FIG. 1). The snap hook 73 is carried by the third strap segment 55 and attaches to the D-ring member 75 (See FIG. 1). D-ring member 75 is attached to the pouch 30 at the intersection of side seam 33 with the upper edge 34. As is discussed with reference to FIG. 8 below, the third strap segment 55 has a second end 76 to which a removable fastener 77 is attached, and includes inner and outer surfaces 78 and 79, respectively. Fastener 77 includes the same components and is formed from the same materials as fasteners 48 and 62, and is used to secure the second end 76 in place against the outer surface 79 of strap segment 55 after the length of strap segment 55 has been adjusted.

Referring again to FIG. 4, the strap assembly 40 also includes a removable pad 80, which is used to enhance the comfort of the strap assembly 40 against the body of the wearer. While the pad 80 may have any shape and be formed from any suitable materials, the pad 80 preferably has a rectangular shape, and includes interior and exterior surfaces 81 and 82, respectively, which are formed from a flexible, durable fabric like that used to cover the cushion 20. Two strips of male hook fasteners 84 and 85 are attached to the interior surface 81 of the pad 80, and are used to maintain the pad 80 in a stationary, tri-folded position around the second strap segment 54 (See FIG. 2). The respective longitudinal axes of strips 84 and 85 are preferably positioned parallel to each other and to a longitudinal axis of the pad 80, which enhances the ability of the strips 84 and 85 to maintain the pad 80 in its tri-folded position around strap segment 54. Although the pad 80 may be positioned around the waist strap 42, first strap segment 53 or third strap segment 54, the pad 80 is preferably positioned around strap segment 54 at a location that generally overlies the clavicle on the uninjured side of the wearer's upper torso. Positioning the pad 80 in this location provides additional support and padding to protect the wearer from fatigue and irritation caused by strap segment 54 as it supports the weight of the wearer's abducted forearm and cooperates with the other components of the shoulder strap assembly 40 to draw that weight away from the wearer's neck.

Referring again to FIG. 4, the abduction device 10 also includes a storage strap 90. The strap 90 is preferably formed from the same materials as waist strap 42 and first, second and third strap segments 53, 54 and 55, respectively. The strap 90 includes an inner surface 91, and also has first and second ends 92 and 93 to which a respective one of two identical patches of male hooks 94 are attached.

Figure 5:
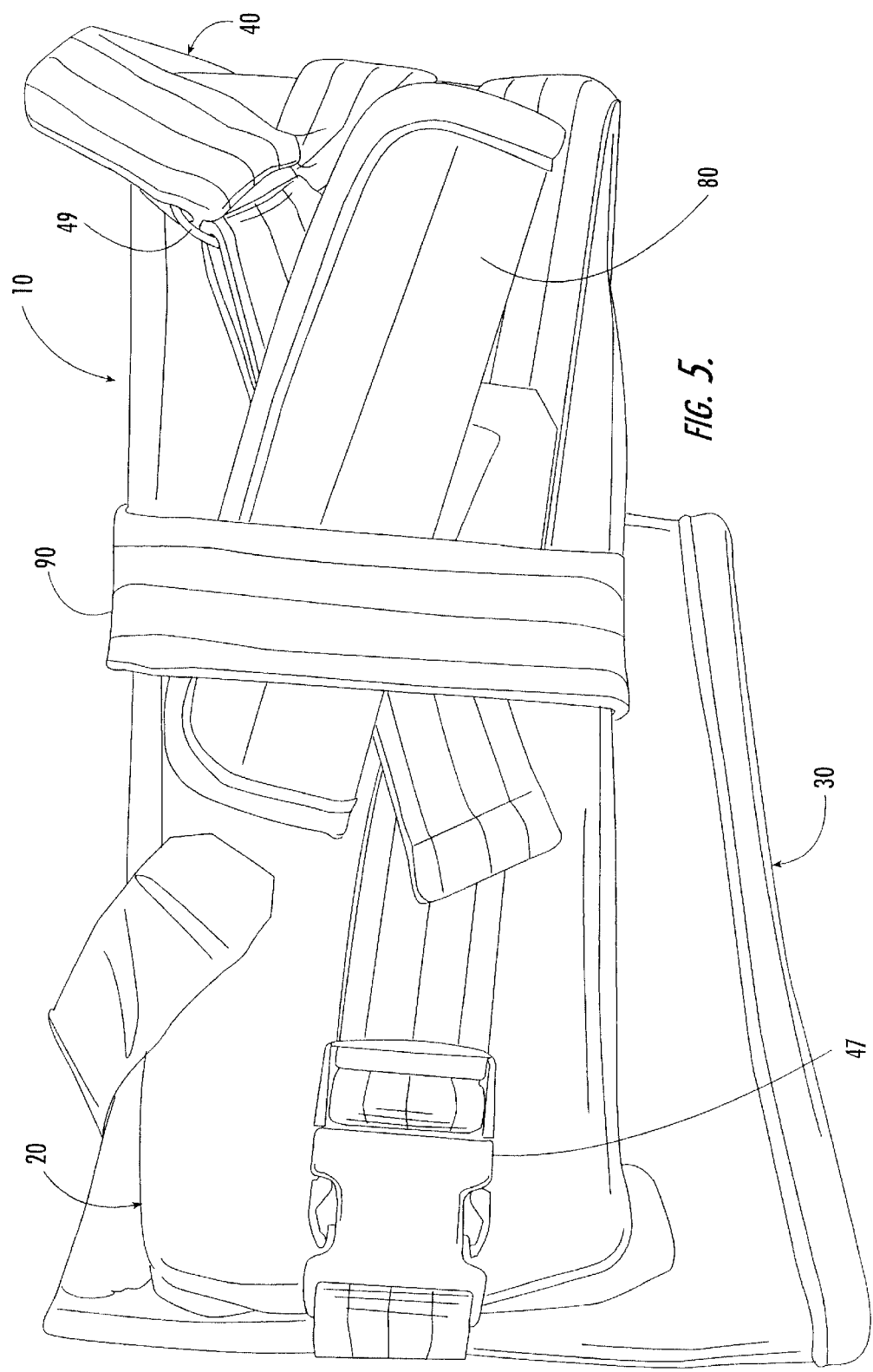
FIG. 5 is a front elevation of the shoulder abduction sling according to FIG. 1 and placed in a folded storage position.

Referring now to FIG. 5, when the abduction device 10 is not in use, the storage strap 90 may be used to hold the pouch 30 and strap assembly 40 in a compact, folded position against the cushion 20 so that the device 10 may be conveniently stored. Alternatively, when the abduction device 10 is to be worn, the storage strap 90 is removed from the device 10, which allows the remaining components of the device 10 to be unfolded so that the device 10 may be positioned on the wearer. Referring again to FIG. 1, once the device 10 is in place on the wearer's body, the first end 92 of strap 90 is connected to the front panel 31 of the pouch 30. The second end 93 is passed over the abducted forearm and the opposing upper edges 34 of pouch 30, and is connected to the back panel 32. The hooked surface of each patch 94 cooperates with the fibrous surface of the pouch 30 to maintain the strap 90 in place. Connecting the storage strap 90 to the pouch 30 in this manner not only ensures that the strap 90 will not be misplaced while the device 10 is being worn, but also ensures that the wearer's forearm will not accidentally slide forward within the pouch 30 and pass through the open end 37.

Referring now to FIGS. 6 through 9, the manner in which the abduction device is used to support an arm and shoulder in an abducted position is illustrated. Given the painful and serious nature of the injuries and conditions that typically require abduction to aid the healing process, it is recommended that the wearer of the device 10 does not attempt to position the device 10 on him or herself without assistance, as such an attempt significantly enhances the risk that additional injury to the pelvic girdle will occur. It is instead preferable that at least one healthcare provider or other individual trained in the proper technique for fitting the device 10 assist in positioning the device 10 around the wearer's upper torso. Ideally, one trained individual should be utilized to support the wearer's arm in a stationary, abducted position throughout the fitting process, while a second trained individual positions the device 10 in the proper position relative to the wearer's torso and abducted arm and secures the device 10 in place using the adjustable strap assembly 40.

Figure 6:
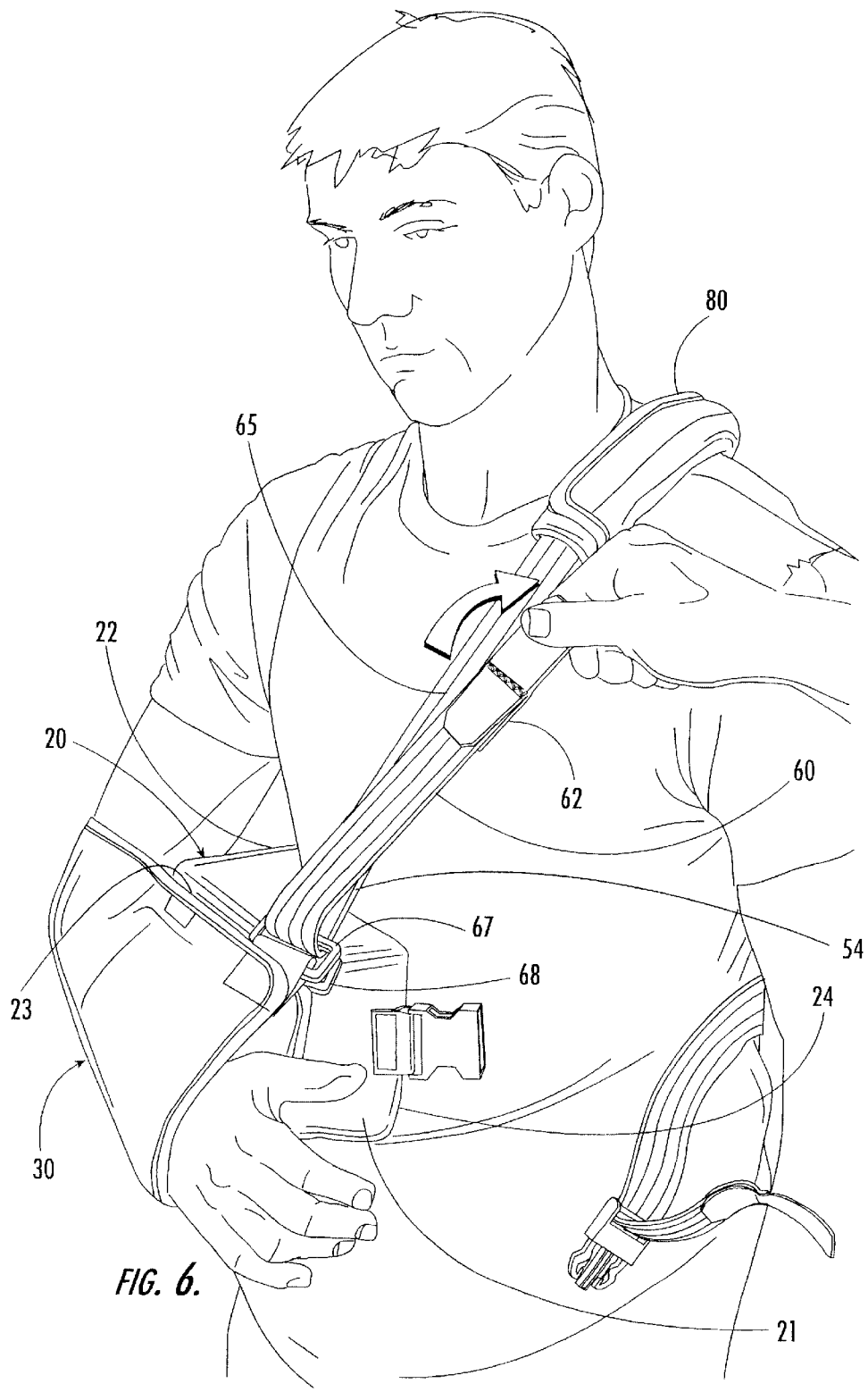
FIG. 6 is an environmental perspective view of the shoulder abduction sling illustrating the manner in which the shoulder strap is positioned over the shoulder and secured in place relative thereto.

Referring now to FIG. 6, to use the device 10 to maintain an injured shoulder in an abducted position, the injured forearm is placed within the pouch 30 in the manner shown, and is held in a preselected abducted position away from the torso so that the cushion 20 can be placed between the abducted arm and the lower torso. While the cushion 20 may be placed in any position relative to the torso and abducted arm, the cushion is preferably so that the humerus is abducted between 10 and 15 degrees away from the wearer's body. As is shown in FIG. 6, the posterior surface 24 of the cushion 20 is preferably positioned against the torso so that the lateral surface 21 lies generally adjacent the umbilicus and the lateral surface 22 lies generally between the elbow of the abducted arm of the wearer. This permits the anterior surface 23 of the cushion 20 to extend along the longitudinal axis of the abducted forearm so that the intersecting edge of the anterior surface 23 and lateral surface 22 is received within the bend of the wearer's elbow. This also permits a maximum surface area of the cushion 20 to be utilized in providing support to the arm as the cushion 20 maintains the arm in the abducted position.

As is shown in FIG. 6, once the cushion 20 and pouch 30 are positioned relative to the arm and torso, the pad 80 is folded around the second strap segment 54 and the second strap segment 54 is brought over the wearer's uninjured shoulder. The second end 60 is then threaded through loops 68 and 67, respectively, and the length of the second strap segment 54 and the position of the pad 80 are adjusted. Once the strap segment 54 and pad 80 are properly oriented, the fastener 62 is attached to the outer surface 65 of the strap segment 54 by moving the fastener 62 toward the outer surface 65 in the direction shown.

Figure 7:
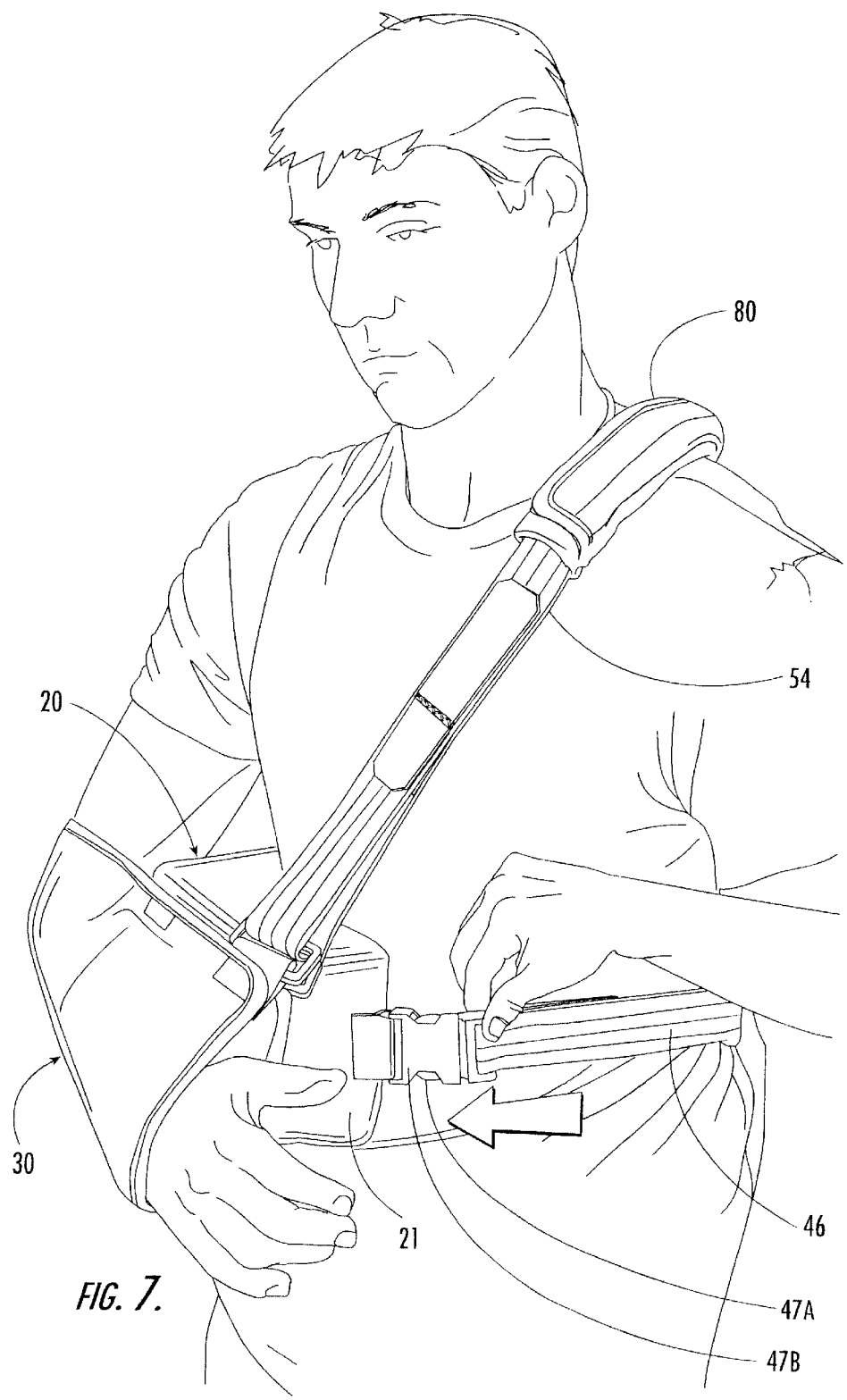
FIG. 7 is an environmental perspective view of the shoulder abduction sling illustrating the manner in which the waist strap is positioned around the waist and secured in place relative thereto.
Figure 8:
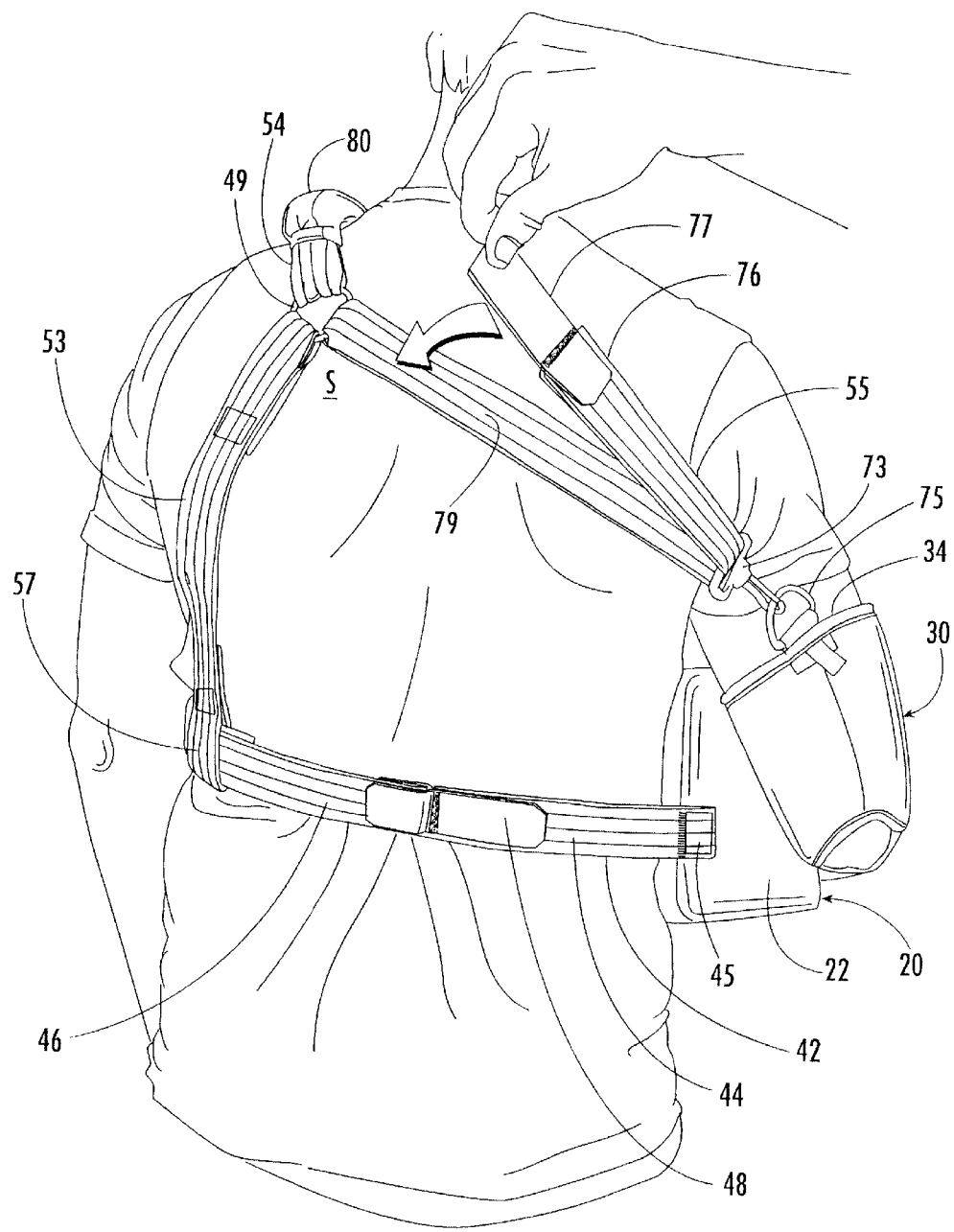
FIG. 8 is an environmental perspective view of the shoulder abduction sling illustrating the manner in which the length of a strap is adjusted.
Figure 9:
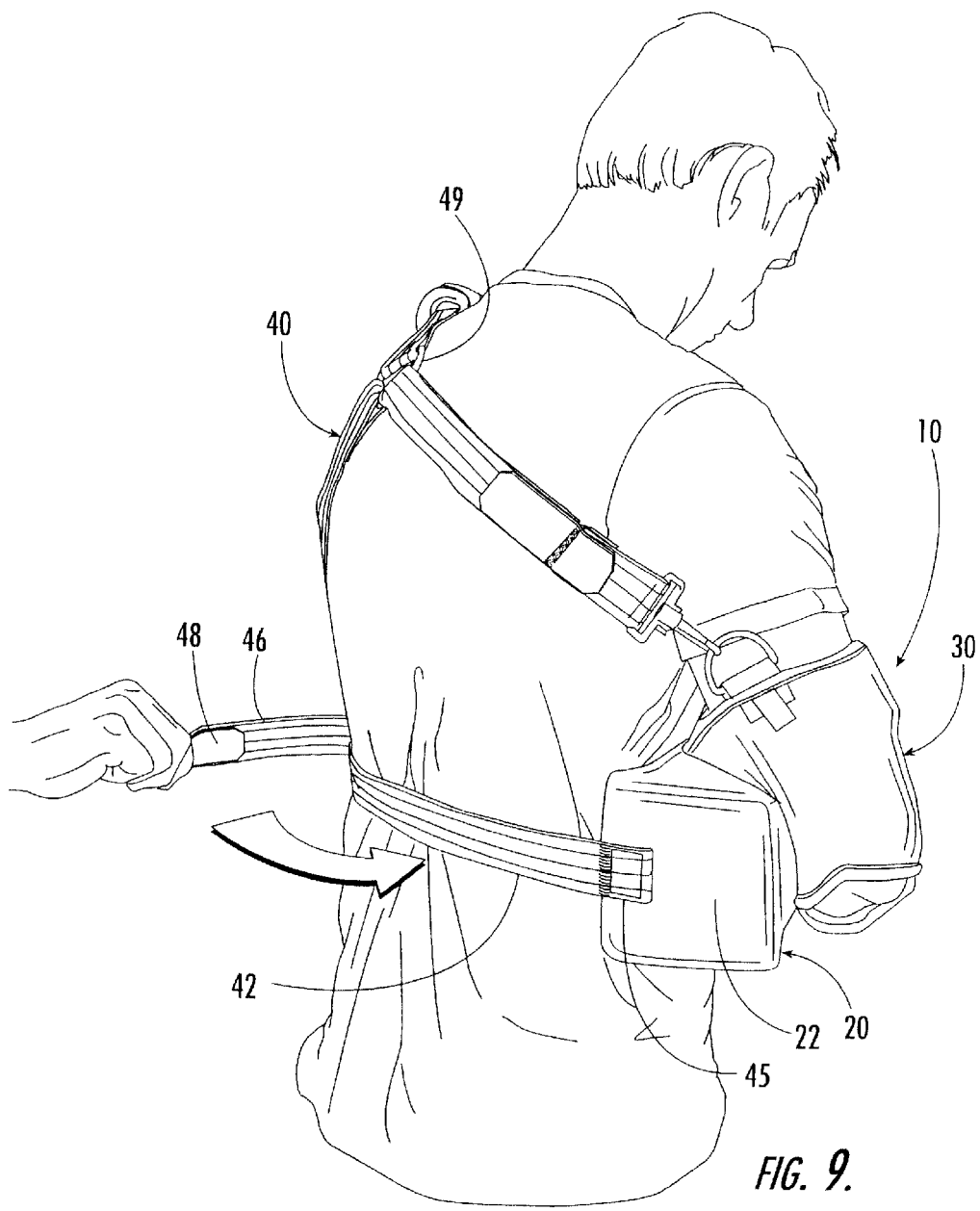
FIG. 9 is an environmental perspective view of the shoulder abduction sling illustrating the manner in which the length of the waist strap is adjusted.

Referring now to FIG. 7, after the second strap segment 54 has been properly connected to the pouch 30, the second end 46 of the waist strap 42 is brought around the back of the wearer and beneath the uninjured arm so that the tongue member 47A and clasp 47B of the slide release buckle 47 can be joined together. As is shown in FIG. 8, fastener 48 is used to connect the second end 46 to the outer surface 44 of the waist strap 42 after the length of the waist strap 42 has been adjusted. FIG. 9 illustrates the manner in which the second end 46 and fastener 48 are pulled back around the wearer's back, away from the lateral surface 21 of the cushion 20, and toward lateral surface 22, which draws the cushion 20 against the wearer's torso and allows the length of waist strap 42 to be adjusted.

Referring now to FIG. 8, the manner in which the fastener 48 connects to the outer surface 44 of waist strap 42 after the adjustment process is completed is shown. Once the waist strap 42 is in position, the ring member 49 is placed over the uninjured scapula "S" of the wearer, and the second end 57 of the first strap segment 53 is moved along the length of the waist strap 42 until the first strap segment 53 is positioned so that it extends between the waist strap 42 and the ring member 49 approximately parallel to the wearer's spinal column. The third strap member 55 is then positioned across the wearer's back so that it extends diagonally from the ring member 49 to the upper edge 34 of the pouch 30. This permits the snap hook 73 through which the second end 76 of the strap segment 55 has been threaded to be connected to the D-ring member 75 on the pouch 30. The length of the strap segment 55 is then adjusted to ensure that the abducted forearm, elbow and upper arm are properly aligned with the clavicular complex. The fastener 77 is then attached to the outer surface 79 to hold the strap segment 55 in place. Positioning the first strap segment 53 and ring member 49 in offset relation to the wearer's spinal column while simultaneously extending third strap member 55 diagonally across the wearer's back to the pouch 30 results in an even distribution of the weight of the wearer's abducted arm across the wearer's back, and creates a laterally-directed force on the second strap segment 54 that pulls the second strap segment 54 away from the wearer's neck. This in turn significantly decreases the pain and fatigue experienced by the wearer while the device 10 is being worn.

Figure 10:
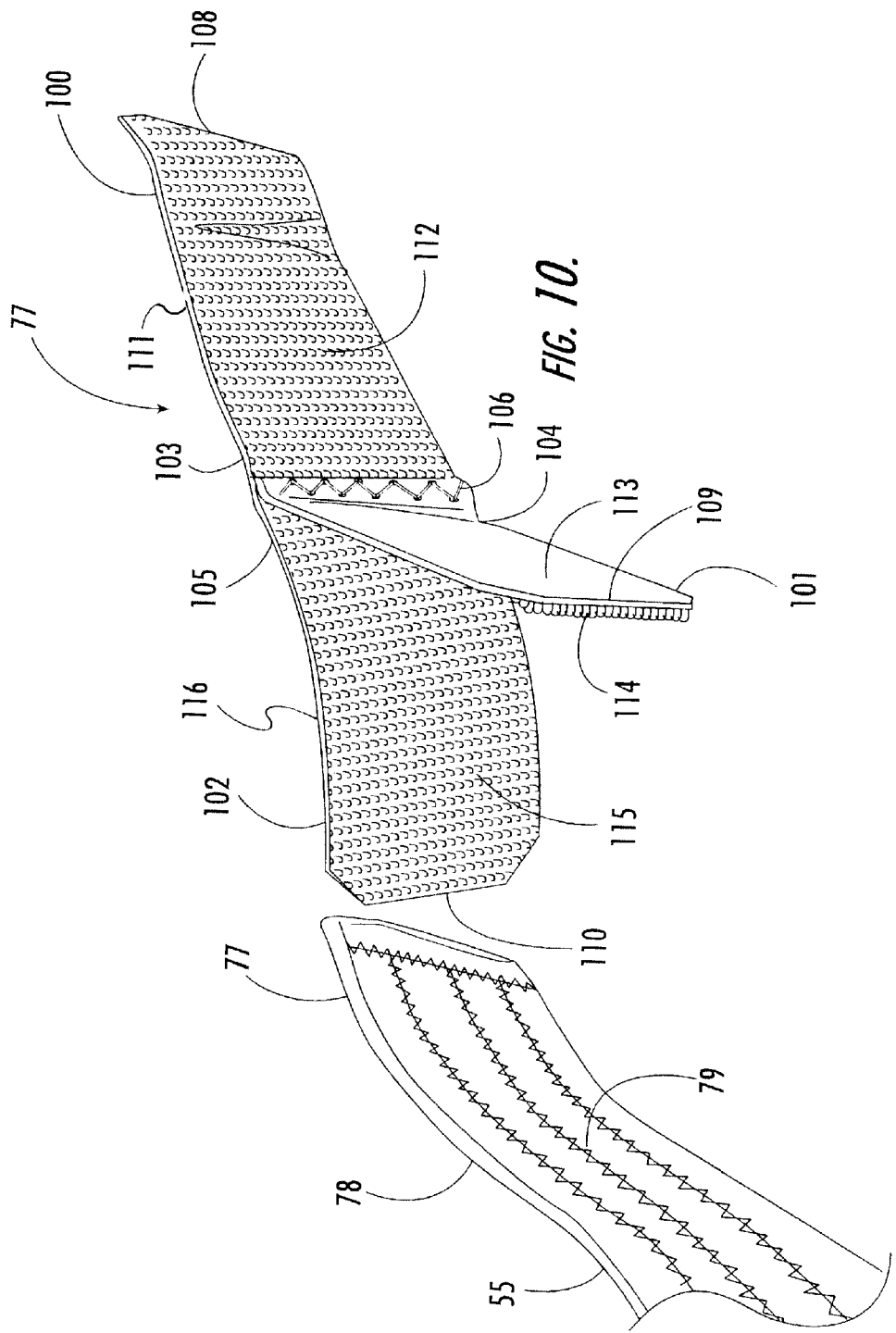
FIG. 10 is a perspective view of one of the fasteners included on the shoulder abduction sling prior to attachment to the end of a strap.

Referring now to FIG. 10, the fastener 77 is shown removed from the second end 76 of the strap segment 55. Because fastener 77 is made from the same materials and includes the same components as fasteners 48 and 62, fastener 77 serves as a representative sample of the structure of fasteners 48 and 62.

As is shown in FIG. 10, the fastener 77 is formed from three separate patches of male hook fasteners 100,101 and 102. First ends 103, 104 and 105 of respective patches 100, 101 and 102 are connected together by a seam 106, which causes the respective second ends 108,109, and 110 of patches 100,101 and 102 to extend radially outwardly away from the seam 106.

While each patch 100,101 and 102 includes two surfaces 111,112; 113,114; and 115,116; respectively, only one of the surfaces of each patch 100,101 and 102 is covered with male hook fasteners. This permits the second end 77 of the third strap segment 55 to be sandwiched in between the patches 101 and 102 so that the hooks on surfaces 114 and 115 cling to the outer and inner surfaces 79 and 78, respectively, of strap segment 55. Surface 112 of patch 100 is also covered with male hooks. Patch 100 is positioned so that the hooked surface 112 faces the smooth surface 113 of patch 101. The hooked surface 112 of patch 100 may then be attached to the complementary outer surface 79 of the third strap segment 55 to maintain the segment 55 in a stationary position while the device 10 is worn. Fasteners 48 and 62 are attached to the respective second ends 46 and 60 in an identical manner.

Figure 11:
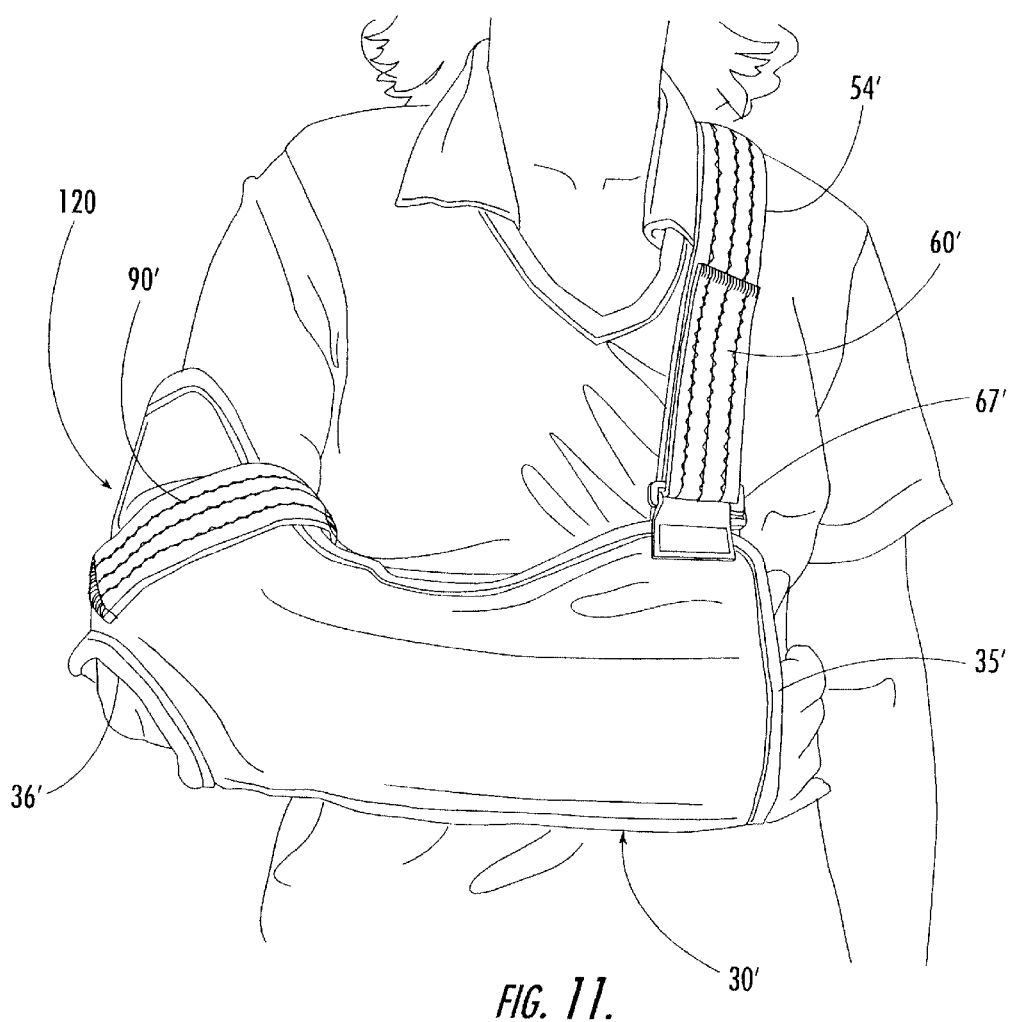
FIG. 11 is an environmental perspective view illustrating the front of a shoulder abduction sling according to an alternative embodiment of the invention during use.

Referring now to FIG. 11, an abduction device according to an alternative embodiment of the invention is illustrated and shown generally at reference numeral 120. Because the device 120 includes several of the same components and is formed from the same materials as the components of device 10, like components are shown using prime reference numerals. The primary difference between devices 120 and 10 is that device 120 lacks the pad 80 and complementary male or female hook-and-loop fasteners 71 and 72 of the device 10. Furthermore, unlike device 10, which utilizes fasteners 48, 62 and 77 to attach the respective second ends 46, 60 and 76 of straps 42, 54 and 55 to the appropriate locations on device 10, device 120 utilizes complementary patches of male hook fasteners to attach the second ends 46', 60' and 76' to outer surfaces 44', 65' and 79', respectively.

An adjustable abduction device is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. An adjustable abduction apparatus, comprising:
   (a) a cushion for being received against the torso of the wearer;
   (b) an open-sided sling pouch having front panel and a back panel for receiving a limb of the wearer therein, said sling pouch having opposing upper edges that are foldable against and removably fixed to one another, said sling pouch releasably attached to said cushion and cooperating therewith for maintaining the limb and shoulder of the wearer in an abducted position;
   (c) an elongate fastener having two opposing hooked surfaces for releasably connecting a complementary fibrous anterior surface of said cushion and a complementary fibrous exterior surface of said back panel of said sling pouch, said elongate fastener extending parallel with respect to said cushion and said back panel; and
   (d) a support assembly for immobilizing the limb and shoulder in the abducted position and distributing the weight of the abducted limb evenly across the torso of the wearer, said support assembly including:
      (i) a waist strap carried by the cushion for releasably securing the cushion against the torso; and
      (ii) a back strap interconnecting the waist strap and the sling pouch and extending therebetween along the back generally parallel to the spinal column for providing stabilizing support to the sling pouch for maintaining the limb and shoulder in the abducted position.

2. An abduction apparatus according to claim 1, and including a shoulder strap interconnecting said back strap and the sling pouch and extending therebetween generally diagonally across the spinal column of the wearer.

3. An abduction apparatus according to claim 2, wherein the waist strap is carried by the cushion for releasably securing the cushion against the torso.

4. An abduction apparatus according to claim 3, wherein said waist strap comprises an elongate strap having an outer surface, a first end connected to a first lateral surface of the cushion, and a second end releasably connected to a second opposing lateral surface of the cushion for holding the cushion in place against the torso of the wearer.

5. An abduction apparatus according to claim 4, and including a first fastener attached to said second lateral surface of the cushion for cooperating with a second fastener carried by the waist strap for holding the cushion in place against the torso of the wearer.

6. An abduction support apparatus according to claim 5, wherein said second fastener comprises a tongue carried by the waist strap and said first fastener comprises a complementary clasp for receiving said tongue therein.

7. An abduction apparatus according to claim 5, and including a third fastener releasably attached to the second end of the waist strap and cooperating with said outer surface of the waist strap for releasably securing the second end of the waist strap thereto.

8. An abduction apparatus according to claim 7, wherein said sling pouch defines a closed end defining a lower opening for receiving the wearer's elbow therethrough and an open end for receiving the wearer's hand therethrough.

9. An abduction apparatus according to claim 8, wherein:
   said sling pouch includes a side edge defining said open end; and
   said opposing upper edges define an upper opening through which the wearer's arm is received for positioning the arm within the pouch.

10. An abduction apparatus according to claim 9, and including a closure strap releasably interconnecting said upper edges for maintaining the wearer's forearm in a stationary position within the pouch.

11. An abduction apparatus according to claim 8, wherein said shoulder strap is releasably connected to the sling pouch adjacent said closed end by a fourth fastener.

12. An abduction apparatus according to claim 11, wherein said fourth fastener comprises a snap hook connected to the shoulder strap and a complementary D-ring connected to an upper edge of the sling pouch adjacent the lower opening and adapted for receiving said snap hook therethrough.

13. An abduction apparatus according to claim 12, wherein the shoulder strap comprises an outer surface and first and second ends, wherein said first end is connected to the back strap, and said second end is received through a complementary opening defined by said snap hook and is releasably attached to said outer surface of the shoulder strap, thereby permitting the length of the shoulder strap to be adjusted.

14. An abduction apparatus according to claim 8, and including a fifth fastener for releasably connecting the back strap to the sling pouch and cooperating therewith for defining the open end of the sling pouch.

15. An abduction apparatus according to claim 14, wherein said upper edge of the sling pouch is integrally formed with a side edge of the sling pouch and cooperates with the side edge and said fifth fastener for defining the open end.

16. An abduction apparatus according to claim 14 or 15, wherein said fifth fastener comprises:
   (i) two loops connected to the upper edge of the sling pouch adjacent the open end, each of said loops adapted for receiving the second end of the back strap therethrough; and
   (ii) a patch of hooked material connected to said second end of the shoulder strap for cooperating with a complementary outer surface of the shoulder strap for permitting the length of the back strap to be adjusted.

17. An abduction apparatus according to claim 14 or 15, and including a sixth fastener attached to an anterior portion of the sling pouch adjacent the upper edge and cooperating with a seventh fastener attached to a posterior portion of the sling pouch adjacent the upper edge for releasably connecting said anterior and posterior portions together, thereby stabilizing movement of the loops of the fifth fastener relative to the back strap.

18. An abduction apparatus according to claim 17, wherein said sixth fastener comprises a patch of hooked material and said seventh fastener comprises a complementary patch of looped material.

19. An abduction apparatus according to claim 17, wherein said sixth fastener comprises a patch of looped material and said seventh fastener comprises a complementary patch of hooked material.

20. An abduction apparatus according to claim 1 or 2, wherein the back strap comprises upper and lower straps having respective first and second ends, said first ends joined together at a common point for being positioned on the wearer's back.

21. An abduction apparatus according to claim 20, wherein said shoulder strap is connected to the back strap at said common point.

22. An abduction apparatus according to claim 21, wherein the common point comprises a ring member.

23. An adjustable abduction apparatus, comprising:
   (a) a cushion for being received against the torso of the wearer for maintaining a limb and shoulder of the wearer in an abducted position relative to the torso;
   (b) an open-sided sling pouch having a front panel and a back panel for receiving the limb therein, said sling pouch having opposing upper edges that are foldable against and removably fixed to one another, said sling pouch releasably attached to said cushion and cooperating therewith for maintaining the limb and shoulder in the abducted position;
   (c) an elogate fastener having two opposing hooked surfaces for releasably connecting a complementary fibrous anterior surface of said cushion and a complementary fibrous exterior surface of said back panel of said sling pouch, said elongate fastener extending parallel with respect to said cushion and said back panel; and
   (d) a support assembly releasably connected to said pouch and cushion for immobilizing the limb and shoulder in the abducted position and distributing the weight of the abducted limb evenly across the torso of the wearer, said support including:
      (i) a waist strap carried by the cushion for releasably securing the cushion against the torso; and
      (ii) a back strap interconnecting said waist strap and the sling pouch and extending therebetween along the back generally parallel to the spinal column of the wearer for providing stabilizing support to the sling pouch, thereby maintaining the limb and shoulder in the abducted position.

24. An adjustable abduction apparatus, comprising:
   (a) a cushion for being received against the torso of a wearer for maintaining a limb and shoulder of the wearer in an abducted position relative to the torso;
   (b) an open-sided sling pouch having a front panel and a back panel for receiving the limb therein, said sling pouch having opposing upper edges that are foldable against and removably fixed to one another, said sling pouch releasably attached to said cushion and cooperating therewith for maintaining the limb and shoulder in the abducted position;
   (c) an elongate fastener having two opposing hooked surfaces for releasably connecting complementary fibrous surfaces of said cushion and said back panel of said sling pouch, said elongate fastener extending parallel with respect to said cushion and said back panel; and
   (d) a support assembly releasably connected to said pouch and cushion for immobilizing the limb and shoulder in the abducted position and distributing the weight of the abducted limb evenly across the torso of the wearer, said support including:
      (i) a waist strap carried by the cushion for releasably securing the cushion against the torso; and
      (ii) a back strap interconnecting said waist strap and the sling pouch and extending therebetween generally parallel to the spinal column of the wearer for providing stabilizing support to the sling pouch for maintaining the limb and shoulder in the abducted position; and
      (iii) a shoulder strap interconnecting said back strap and the sling pouch and extending therebetween across an uninjured shoulder joint and generally diagonally across the spinal column of the wearer.

25. A method of abducting a limb and injured shoulder relative to the torso of a wearer, comprising the steps of:
   (a) providing an adjustable abduction apparatus, including a cushion for being received against the torso of the wearer; an open-sided sling pouch laving a front panel and a back panel for receiving a limb of the wearer therein, the sling pouch having opposing upper edges that are foldable against and removably fixed to one another, the sling pouch releasably attached to the cushion and cooperating therewith for maintaining the limb and shoulder of the wearer in an abducted position; an elongate fastener having two opposing hooked surfaces for releasably connecting complementary fibrous surfaces of the cushion and the back panel of the sling pouch, the elongate fastener extending parallel with respect to the cushion and the back panel; and a support assembly for immobilizing the limb and shoulder in the abducted position and distributing the weight of the abducted limb evenly across the torso of the wearer, the support assembly including:
      (i) a waist strap carried by the cushion for releasably securing the cushion against the torso; and
      (ii) a back strap interconnecting the waist strap and the sling pouch and extending therebetween along the back generally parallel to the spinal column for providing stabilizing support to the sling pouch and maintaining the limb and shoulder in the abducted position;
   (b) positioning the cushion against the torso of the wearer;
   (c) using the waist strap to releasably secure the cushion in place against the torso;
   (d) positioning the limb of the wearer within the sling pouch;
   (e) releasably attaching the sting pouch to the cushion;
   (f) extending the back strap from the waist strap over the uninjured shoulder of the wearer to the sling pouch; and
   (g) connecting the waist strap to the sling pouch.

* * * * *

UNITED STATES PATENT AND TRADEMARK OFFICE
CERTIFICATE OF CORRECTION

PATENT NO.     : 6,659,971 B2                                                          Page 1 of 1
DATED          : December 9, 2003
INVENTOR(S)    : Eric Lee Gaylord It is certified that error appears in the above-identified patent and that said Letters Patent is hereby corrected as shown below:

Column 5,
Line 12, "according, to" should read -- according to --.

Column 11,
Line 12, "having front" should read -- having a front --.

Column 14,
Line 20, "laving" should read -- having --.
Line 49, "sting" should read -- sling --.

Signed and Sealed this

Twentieth Day of January, 2004

JON W. DUDAS
*Acting Director of the United States Patent and Trademark Office*